US00PP27197P3

(12) United States Plant Patent
Ryan-Bohac

(10) Patent No.: US PP27,197 P3
(45) **Date of Patent: *Sep. 27, 2016**

(54) SWEETPOTATO PLANT NAMED 'CX-1'

(50) Latin Name: ***Ipomoea batatas* (L.) Lam.**
Varietal Denomination: CX-1

(75) Inventor: Janice Ryan-Bohac, North Charleston, SC (US)

(73) Assignee: Carolina Advanced Renewable Energy, LLC, North Charleston, SC (US)

( * ) Notice: Subject to any disclaimer, the term of this patent is extended or adjusted under 35 U.S.C. 154(b) by 752 days.

This patent is subject to a terminal disclaimer.

(21) Appl. No.: 12/590,776

(22) Filed: Nov. 13, 2009

(65) Prior Publication Data

US 2010/0122388 P1 May 13, 2010

Related U.S. Application Data

(60) Provisional application No. 61/114,358, filed on Nov. 13, 2008.

(51) Int. Cl.

| | |
|---|---|
| ***A01H 5/06*** | (2006.01) |
| ***A01H 5/04*** | (2006.01) |
| ***A01G 1/00*** | (2006.01) |
| ***A01G 7/00*** | (2006.01) |
| ***A23L 1/217*** | (2006.01) |

(52) U.S. Cl.
USPC ..... Plt./258
CPC *A01H 5/04* (2013.01); *A01G 1/00* (2013.01); *A01G 7/00* (2013.01); *A23L 1/217* (2013.01); *A23L 1/2175* (2013.01); *Y02E 50/17* (2013.01)

(58) Field of Classification Search
USPC ..... Plt./258, 263.1
CPC ..... A01H 5/04; A01H 5/00; A01H 5/06
See application file for complete search history.

(56) References Cited

U.S. PATENT DOCUMENTS

2010/0120109 A1* 5/2010 Ryan-Bohac ..... 435/161

OTHER PUBLICATIONS

Daifu et al., Sweetpotato varieties decline in China and the prevent practices, *International Workshop on Sweetpotato Decline Study,* pub. Kyushu National Agricultural Experiment Station, Miyakonojo, Japan, pp. 20-26 (2000).
Gitoner, "Potato and Sweetpotato in China: systems, constraints, and potential," Chinese Academy of Agricultural Sciences & International Potato Center Regional Office, Beijing, China, p. 79, 82 (1996).
Grünberg et al., Genotype X Environment interactions for a diverse set of sweetpotato clones evaluated across varying ecogeographic conditions in Peru, *Crop Science,* 45:2160-2171 (2005).
Min, Li Hong, "Sweet Potato Varietal Trial," *Asian Regional Vegetable Research Center.* Proceedings of Training Workshop (1990).
Woolfe, "Sweetpotato an untapped food resource," Cambridge University Press, Cambridge, UK, p. 50 (1992).
Zhi, Xie Yi, "Effect of Potassium on the yield of three sweet potato varieties," *Asian Regional Vegetable Research Center.* Proceedings of Training Workshop (1991).

* cited by examiner

*Primary Examiner* — Kent L Bell
(74) *Attorney, Agent, or Firm* — Linda R. Judge

(57) ABSTRACT

This invention relates to 'CX-1', a new and distinct cultivar of sweetpotato, *Ipomoea batatas*, (L.) Lam. It is a distinct mutant from the sweetpotato variety, 'Xushu 18' from China, where other superior mutant cultivars of 'Xushu 18' have been registered. 'CX-1' is a distinct cultivar with high yield and higher dry matter than 'Xushu 18'. By combining high levels of carbohydrate (mostly starch and some sugars) with high tonnage of roots per acre, 'CX-1' will produce very high levels of ethanol per acre compared to other temperate crops. This type of sweetpotato with its uniquely high dry matter, high starch content, and mealy texture can also be used to produce sweetpotato chips and fries that have significantly less oil than commercially available low dry matter sweetpotato varieties like 'Beauregard'.

6 Drawing Sheets

Latin name of the genus and species of the plant claimed: *Ipomoea batatas* (L.) Lam.

Variety denomination: 'CX-1'.

This invention relates to a new and distinct cultivar of sweetpotato named 'CX-1'.

BACKGROUND OF THE INVENTION

This disclosure relates to a new and distinct variety (cultivar) of sweetpotato named 'CX-1'.

This new variety of sweetpotato (*Ipomoea batatas* (L.) Lam.) was developed by selection of 'Xushu 18', and designated 'CX-1.' It was selected for large roots, very high dry matter content and higher yield. Field tests were conducted in Florida and South Carolina. Although there are a large number of sweetpotato varieties, there is a wide range of appearance, growth parameters, and uses, not a lot is known about the genetics of this crop species. Sweetpotato is the $7^{th}$ largest food crop in the world and is a major food staple in many countries, mostly in the tropics.

Sweetpotatoes are underground storage roots, not tubers. The botanical description of a tuber is a short, thickened portion of an underground stem. The tuber has eyes composed of a ridge bearing a 'scale-like' leaf with tiny meristematic buds in the axial of this scale-like leaf. The sweetpotato is a true root, not an underground tuber that has buds. The anatomy of a storage root is the same as any root, with an additional ability to expand radially to store additional starch and nutrients. The sweetpotato crop is asexually propagated crop from 'seed' roots and plant cuttings.

Currently grown U.S. sweetpotato varieties were developed to be eaten as a highly nutritious and delectable vegetable. This variety type has been bred for specific traits for that use. They produce relatively uniform, attractively shaped storage roots, with dark orange flesh, a sweet, delicious flavor, and a moist texture (from 77% to 81% moisture). The typical size of these roots is from 6 to 16 ounces. The typical fresh weight yields of these varieties will range from 12 to 15 tons of marketable roots per acre.

The sweetpotato variety Xushu 18 is a variety that was publicly released in 1972 from China. It was bred by researchers in Jiangsu Province, China. Xushu 18 was a seedling from a cross from the variety Xindazi and breeding line 52-45. (Gitoner, C. 1996. Potato and Sweetpotato in China: systems, constraints, and potential. International Potato Center. Lima, Peru).

'Xushu 18' has been a popular variety in China, a country that is a major producer of sweetpotatoes. Researchers in China report that during several decades, dozens of new varieties derived by mutation from named varieties have been registered. Researchers in Xuzhou, China report that a single plant resulting from a selection of 'Xushu 18' with superior characteristics was named 'Xu 77-6' and was selected to replace normal 'Xushu 18' (Daifu, M., Hongmin, L., DaPeng, L., and Yi, W. 2000. Sweetpotato varieties decline in China and the present practices. International Workshop on Sweetpotato Decline Study Sep. 8-9 2000. Kyushu National Agricultural Experiment Station. Miyakonojo, Japan.)

'Xushu 18' was not developed as a table vegetable. It was developed for its production of starch and for animal feed. It is not sweet or delicious, but is white fleshed, very bland and very dry,—about 28% dry matter. Commercial yields in China have been reported from 6.88 ton up to 18.5 tons of fresh root weight per acre (Gitoner, 1996). Currently there are no sweetpotato varieties, with high dry matter content, commercially grown in the U.S. for industrial uses such as starch and ethanol.

Starting with the 'Xushu 18', a distinctive, new cultivar was selected and developed for large roots, high dry matter and higher total yield. The original 'Xushu 18' cultivar was obtained from the Plant Genetic Resourses Unit, USDA, ARS, Griffin, Ga. In Spring 2008 'CX-1', was first asexually propagated as cuttings from a single plant selection of 'Xushu 18'. At the test farm in Colleton County, S.C., a single plant was selected for very high yield and propagated there for multiple location testing. After years of field trials, it was determined that a selected high-yielding single plant of Xushu 18, named 'CX-1', produced a higher yield of sweetpotatoes with a higher dry matter content compared to published data on 'Xushu 18' (Table 1).

TABLE 1

| Researcher | Location | Status | Fresh Weight in Tons/ha | Fresh Weight in Tons/A | Root Dry Matter % |
|---|---|---|---|---|---|
| Ma Daifu, CIP | China (mean 19 locations)[a] | Virus Free | 40 | 17.8 | 29 |
| | | Virus Check | 34 | 15.2 | 28 |

TABLE 1-continued

| Researcher | Location | Status | Fresh Weight in Tons/ha | Fresh Weight in Tons/A | Root Dry Matter % |
|---|---|---|---|---|---|
| Gruneberg, Crop Sci | Peru | Mean | 30 | 13.6 | 25 |
| | Tingo Maria | Highest | 70 | 31.5 | NR[a] |
| | La Molina | Lowest | 5 | 2.2 | NR |
| Xie Yi Zhi, ARC | Thailand | Highest | 27 | 12.0 | 26 |
| Ryan-Bohac | USA | FL | | 49.0 | 33 |
| 'CX-1' | USA | SC | | 37.5 | 33 |

[a]NR is Not Reported;

ha = hectors;

A = acres

Wolfgang, G., Manrique, K., Zhang, D, and Hermann, M. 2005. Genotype X Environment interactions for a diverse set of sweetpotato clones evaluated across varying ecogeographic conditions in Peru. Crop Science. 45:2160-2171.

Zhi, X. Y. Effect of Potassium on the yield of three sweet potato varieties. 1991. Asian Regional Vegetable Research Center. Proceedings of Training Workshop.

Daifu, M., Hongmin, L., DaPeng, L., and Yi, W. 2000. Sweetpotato varieties decline in China and the prevent practices. International Workshop on Sweetpotato Decline Study Sep. 8-9, 2000. Kyushu National Agricultural Experiment Station. Miyakonojo, Japan.

Sweetpotato roots of 'CX-1' can be used to produce both starch and fuel ethanol. Estimates of at least 1500 gallons per acre of sweetpotatoes were based on field tonnage per acre, and on laboratory tests of the amount of ethanol produced per ton of dry matter from storage roots. Sweetpotato roots of 'CX-1' were also used to make chips and fries. The high dry-matter 'CX-1' roots are more suited to making chips and fries than those made from the sweet, watery-textured vegetable types of sweetpotato like the leading U.S. variety, 'Beauregard', (19-20% dry matter). The dry matter content of the 'CX-1' cultivar is at least 32%. In contrast, commercial vegetable type sweetpotatoes cultivars have a dry matter content that ranges from 19 to 23%. The texture of the 'CX-1' is dry and mealy in contrast to vegetable types that are moist and sweet with visible syrup in the flesh. The chips made from 'CX-1' were crisp, and light in color, similar to a commercial chip made from the white potato. (FIG. 5). Both the 'CX-1' chips and fries with high dry matter take up significantly less oil and were less bitter than these products made from the white potato.

When properly cured and stored at 50° to 60° F., the 'CX-1' variety can store up to one year. Long-term storage is a genetically controlled trait and a requirement for any successful cultivar in the temperate zones of agricultural production like the U.S. This is in contrast to typical tropical dry fleshed varieties that will deteriorate very quickly in storage. The asexual reproductions run true to the original sweetpotato and to each other in all respects.

Samples of the 'CX-1' variety will be deposited and maintained.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED BOTANICAL DESCRIPTION

Figure 1:
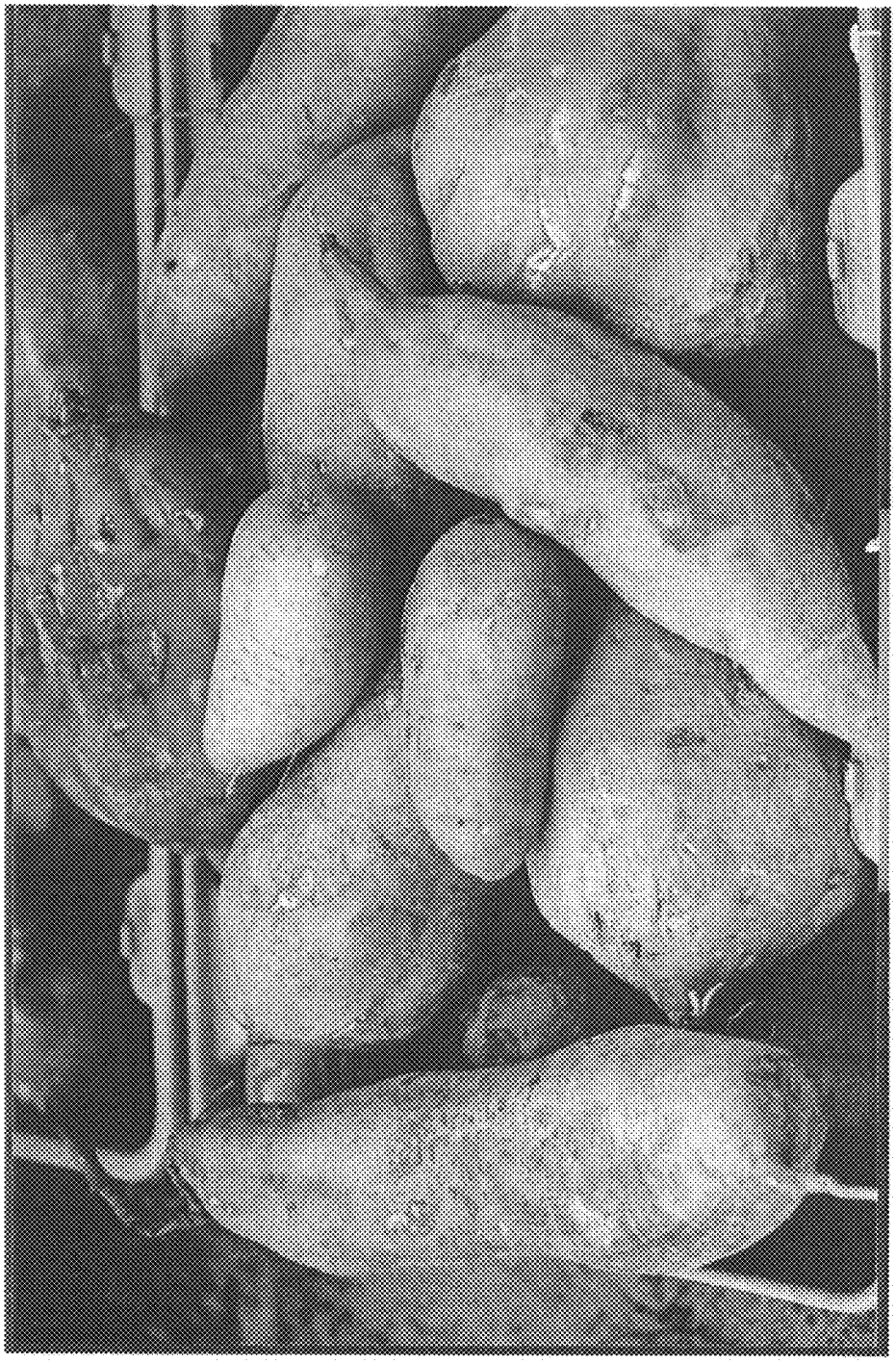
FIG. 1 is a photograph of a flat of rose-skinned, large roots from 'CX-1' sweetpotatoes.

Sizes: 'CX-1' produces large to very large storage roots from 1 pound up to 17 lbs (FIG. 1).

Figure 2:
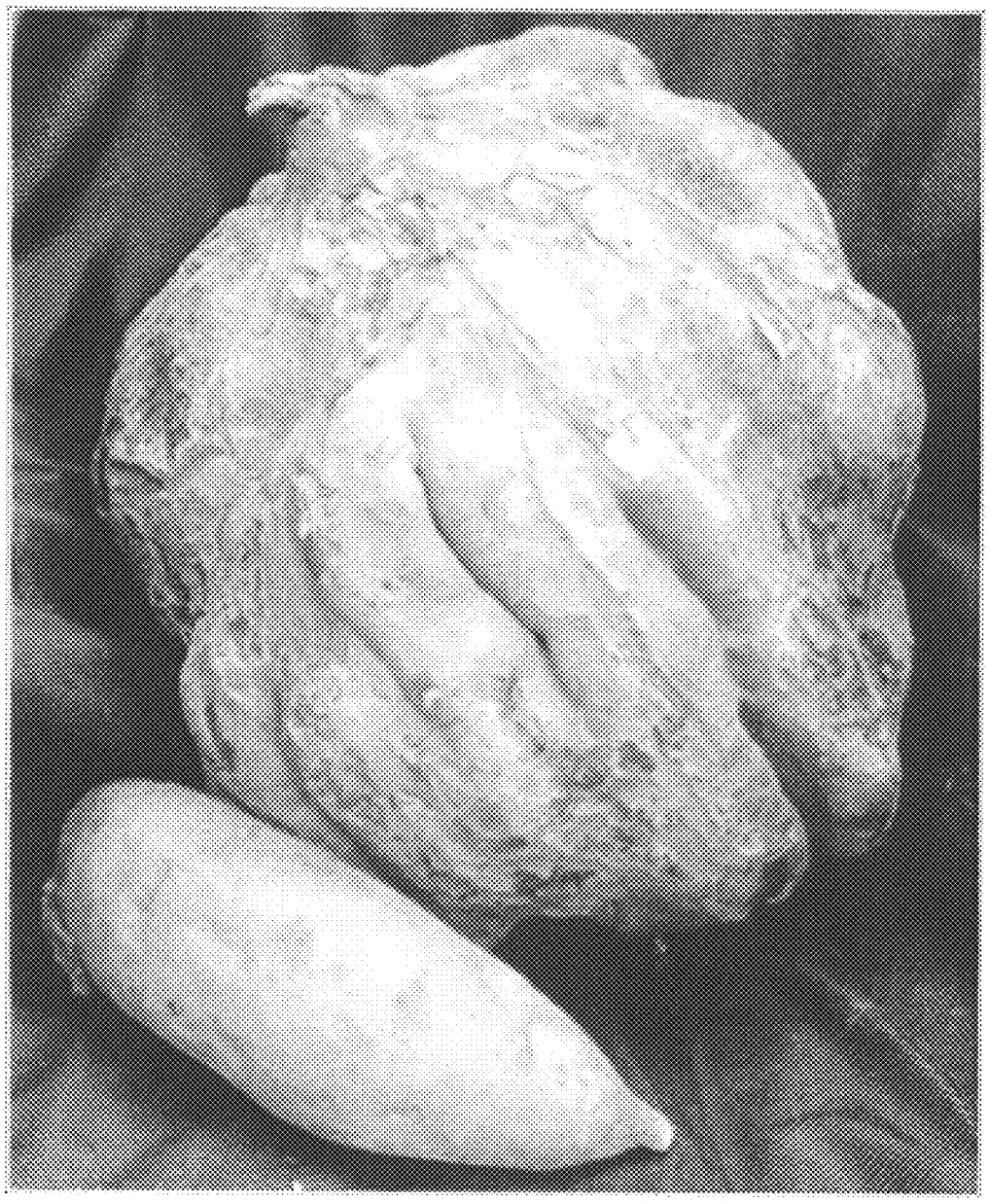
FIG. 2 is a photograph of a very large (17 lbs.) "turnip" shaped 'CX-1' sweetpotato and an 8 ounce copper-skinned 'Beauregard' sweetpotato (accounts for 90% of U.S. commercial market).

Growth: The storage roots initiate at about 45 days after planting. The large roots have a smooth, oblong, blocky shape. The very large roots are deeply grooved with a "turnip" type shape (FIG. 2).

Root color and texture: The storage roots have a medium rose-hued skin that is smooth and attractive on the smaller roots and is rougher and non-uniform on the very large roots. The internal flesh of the storage roots is light yellow with a uniform, starchy appearance. The color analysis of 'CX-1' skin and flesh was performed using the charts—from the Munsell Book of Color, Matte Finish Collection (1976). The Munsell designation is given as hue (such as Red Purple or RP 5.0, Munsell value or V and Munsell chroma, C written as H V/C. The skin color of the storage root is a pale violet red with a Munsell value (H V/C) of 7.5 RP 5.5/6. The flesh color is a light yellow with a Munsell Value of 7.5Y 9/2. The sprouts on the storage root are from 3 cm to 10 cm long, and are dark purple on the base and tip (Munsell value of 10P 4/4 and pale purple in the middle (Munsell value of 10P 9/2).

Figure 3A:
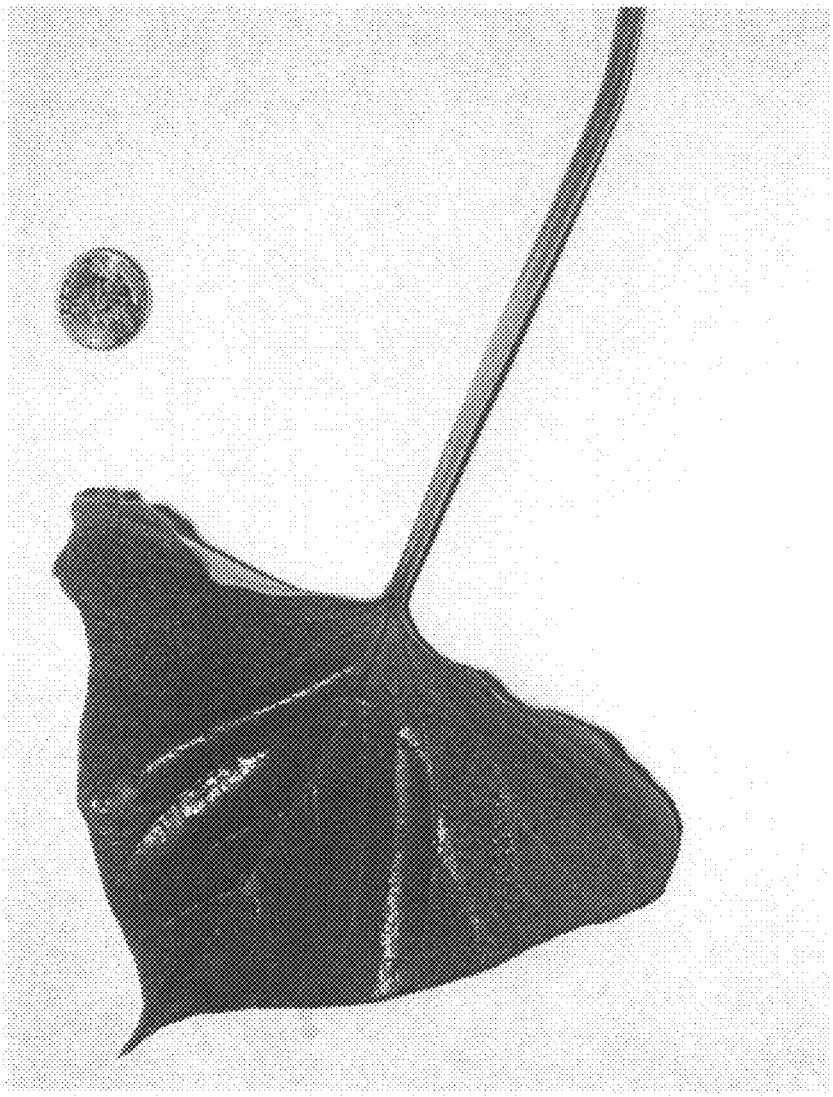
FIGS. 3A and B are photographs of (A) the upper side of a 'CX-1' leaf; and (B) the underside of a 'CX-1' leaf.
Figure 3B:
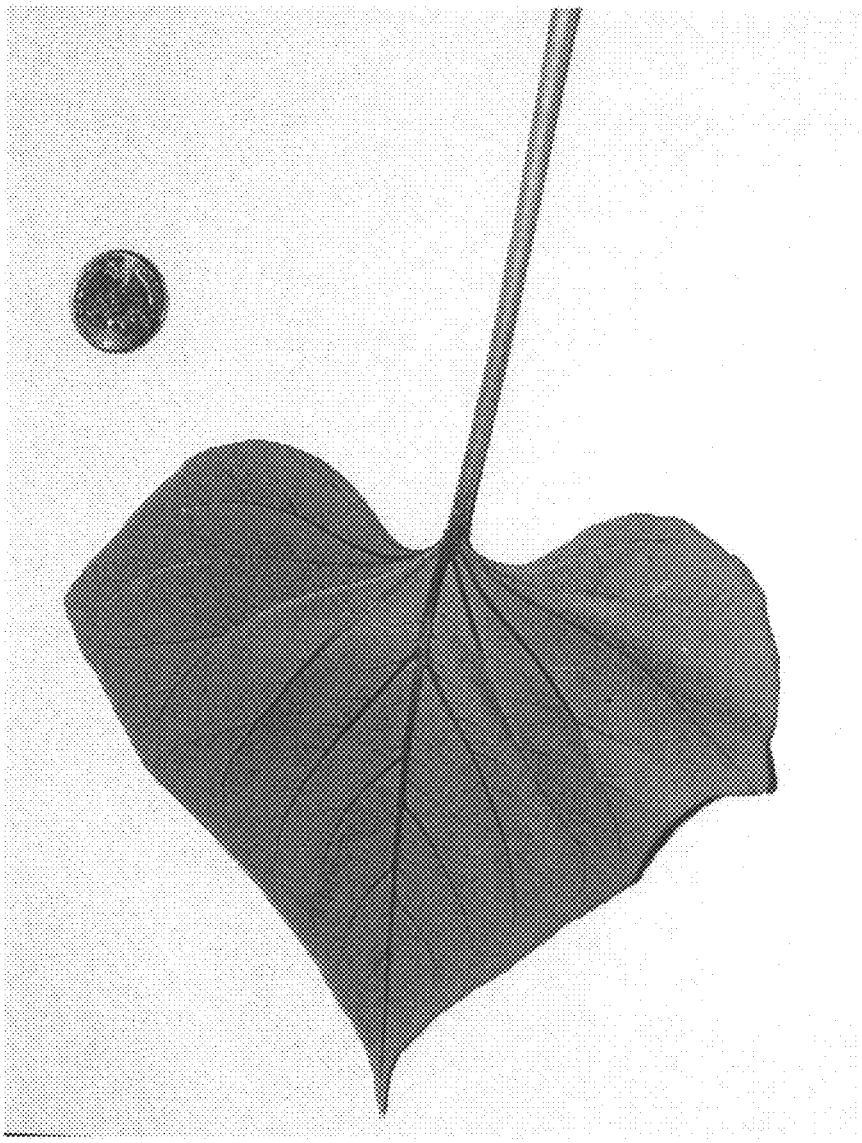

Leaves: Leaves of the 'CX-1' variety are a medium green, cordate-shaped leaf with a purple juncture where the base of the leaf blade meets the petiole and the veins are often purple from the juncture grading to green at the leaf outer edges with slight triparte lobing and an acute apex. The base of the mature leaf is approximately 14 cm wide, and the length from base to the apex is approximately 13-15 cm. The top side of the leaf is medium green yellow (Munsell value of 7GY 4/4) and the bottom side of the leaf is a paler green yellow (Munsell value of 5GY 5/4). The bottom side of the leaf has a dark red purple (5RP 4/6) juncture where the base of the leaf blade meets the petiole. The veins on the abaxial side of the leaf are dark red purple (Munsell value of 5RP 4/6) from the juncture grading to a pale red purple (5RP 7/4) to the leaf outer edges (FIGS. 3A and 3B). The leaf is petiolate, and the length of the petiole is from 22 to 24 cm long, 0.4 cm wide and is a medium green yellow in color (Munsell 5GY 7/6). At the juncture of the petiole attachment to the vine, the juncture is a dark red purple (Munsell 5RP 4/6).

Figure 4:
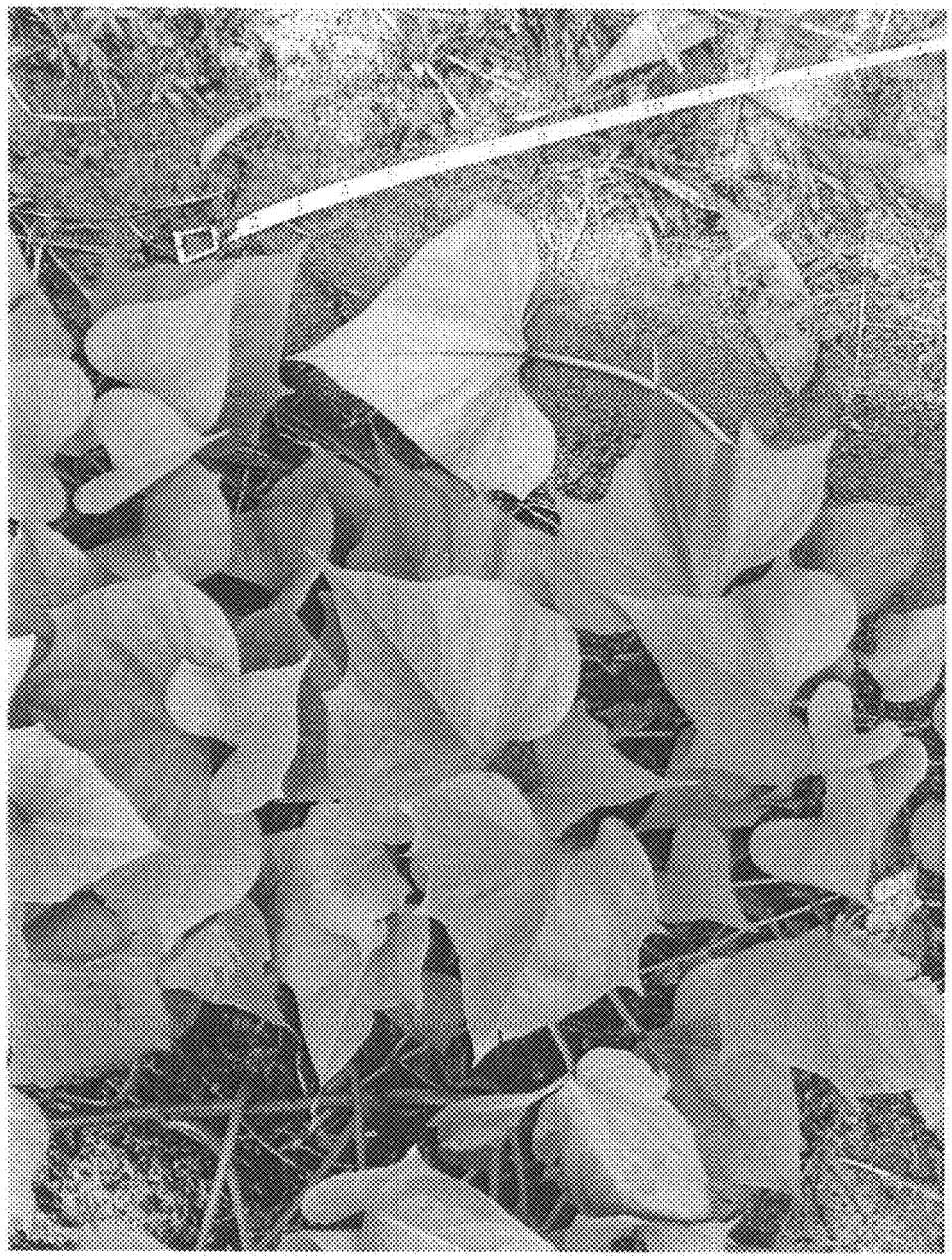
FIG. 4 is a photograph looking down on a planting of 'CX-1' sweetpotatoes.
Figure 5:
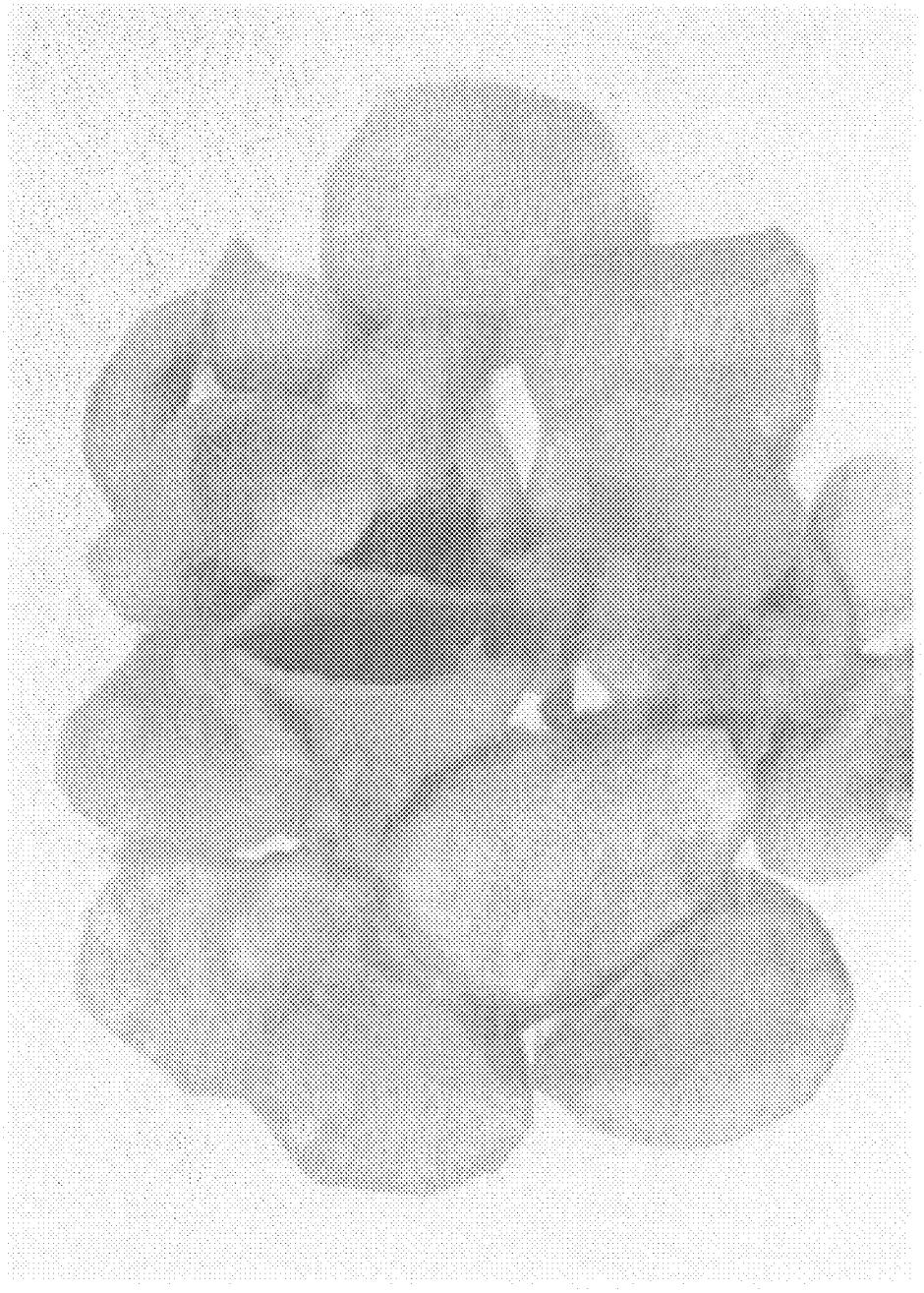
FIG. 5 is a photograph of chips made from 'CX-1' sweetpotatoes.

Vines: The cultivar makes a vigorous vine longer and more robust than 'Beauregard', the leading US sweetpotato variety (FIG. 4). The vine length 60 days after planting in the field ranges from 80 to 120 cm, with a width of 0.6 cm. The internode length ranges from 5 to 6 cm. The vine is a medium green yellow, with a Munsell value of 5GY 7/6.

Flowers: The flowers of the 'CX-1' cultivar are rarely seen. The following observations were based on one flower examined. The flower is borne singularly on a long, green (5GY 8/6) peduncle 8-12 cm long, ascending vertically from the leaf axil of the vines. The flowers have 5 united sepals attached to the base of the corolla. The sepal color is a medium green—5GY 8/6—and the sepals have an elliptic shape with an acute apex. The corolla tube is made up of five petals fused into a lavender, funnel-shaped corolla tube 10P 9/11 of about 5 cm long, and a light purple throat 10P 8/4. The limb or top of the corolla tube is the same color as the outer lube, lavender 10P 9/11, and has a round or rotate shape.

Compared to the leading U.S. cultivar 'Beauregard', the 'CX-1' cultivar produces a larger number of early emerging sprouts, similar to the heirloom cultivar, 'Porto Rico'. The production of a large number of early sprouts will ensure the cultivar will produce the large number of cuttings needed for commercial or industrial propagation of a sweetpotato cultivar.

PRODUCTION OF THE 'CX-1' CULTIVAR

Horticultural methods were developed that differed from standard sweetpotato methods, in order to maximize the yield of 'CX-1'. The standard spacing for vegetable sweetpotato plants is 9 inches apart in the beds, the spacing developed for 'CX-1' was 12 inches apart, which allowed the roots to grow larger. A mechanical pocket transplanter made in Holland, Mich. was used to plant cuttings approximately 10 inches in length. All plots were watered through the transplanter, and occasionally supplemented with irrigation the first 30 days. The remainder of the season, the crop received only normal rain. In order to maximize yield, the 'CX-1' plants were transplanted in late April or May and allowed to grow until the vines were killed by frost. The vegetable sweetpotatoes are harvested at 90 to 100 days after planting. In contrast, sweetpotatoes of the 'CX-1' cultivar are harvested 150 to 180 days after planting (or until the first major frost).

Soil samples were submitted for soil testing. In all trials run in South Carolina and Florida, it was found that the 'CX-1' performed well on sandy loam soils that were low in organic matter. It is expected that the variety would perform well throughout the Coastal Plain soils that are found from southern New Jersey to Florida, and the southern counties in Alabama, Mississippi, Louisiana and East Texas. Soil tests for sweetpotato production in this type of soil recommend 90 lbs of Nitrogen, 110 lbs of Phosphorus and 110 lbs of Potash per acre. It was discovered that the highest yield of 'CX-1' used half of the recommended Nitrogen—45 lbs of Nitrogen per acre. Also added was recommended rate of 110 lbs per acre of Phosphorus and Potash combined with micronutrients—5 lbs of sulfur, 0.38 lbs of Boron, 10 lbs of Manganese and 0.13 lbs of Copper per acre. Also used was 1.5 pints per acre of a weed-control herbicide and a grass herbicide at 1 pint per acre. Insecticides were sprayed as needed. No fungicides or nematacides were required. In multiple locations and years, the 'CX-1' variety did not appear to be susceptible to soil insects, root knot nematodes or diseases like *Fusarium*, soil rot, etc. The variety has not been screened under standard conditions to determine if it has the level of resistance to pests or pathogens like the multiple pest resistant cultivars like 'Liberty' or 'Regal'.

In field trials the yield at 120 and 180 days after planting was found to be 12 tons to 16 tons of dry matter per acre, respectively. Samples of the sweetpotatoes were sent to a laboratory in Muscle Shoals, Ala. and to a laboratory, in Livermore, Calif., for a chemical analysis. It was found that the 'CX-1' roots were approximately 33% dry matter. This dry matter was found to be 86% starch, which is readily converted to fuel ethanol in the process. Two commercially important traits make 'CX-1' advantageous for fuel ethanol production and clearly differentiate 'CX-1' as a new variety derived from Xushu 18. One key fact that indicates 'CX-1' is a stable mutant of Xushu 18, is that 'CX-1' roots have dramatically higher dry matter 33%. In contrast the parent clone, 'Xushu 18', has 27-29% dry matter. Also yield is higher in 'CX-1', fresh weight ranges from 37.5 to 49 tons per acre and (dry weight from 12 to 16 tons per acre). Published fresh weight data for 'Xushu 18' from China, Peru and Thailand have average values of 17.8, 13.6, and 12.0 tons of fresh weight per acre, respectively. (Daifu, M., Hongmin, L., DaPeng, L., and Yi, W. 2000. Sweetpotato varieties decline in China and the prevent practices. International Workshop on Sweetpotato Decline Study Sep. 8-9 2000. Kyushu National Agricultural Experiment Station. Miyakonojo, Japan.; Wolfgang, G., Manrique, K., Zhang, D, and Hermann, M. 2005. Genotype X Environment interactions for a diverse set of sweetpotato clones evaluated across varying ecogeographic conditions in Peru. Crop Science. 45:2160-2171. Zhi, X.Y. Effect of Potassium on the yield of three sweet potato varieties. 1991. Asian Regional Vegetable Research Center. Proceedings of Training Workshop.)

TABLE 2

A Compositional analysis of 'CX-1' variety

| Component | Test Values % of DM |
|---|---|
| Total Solids | 100 |
| Starch[a] | 73.8 |
| Glucose, Maltose, Maltotriose[b] | 0 |
| Protein | 2.45 |
| Fat | 1.86 |
| Ash (at 550° C.) | 2.89 |
| Remainder (fiber, non-starch polysaccharides and lignin)[c] | 19.0 |

[a]Starch content analyzed by AOAC Enzymatic analysis method Number (AOAC 979.1/AACC76.11)
[b]Glucose, Maltose, and Maltotiose are estimated by HPLC PRAJ Standards method
[c]Fiber and other organic matter is extrapolated by the difference in weight method Woolfe, J. 1992. Sweetpotato an untapped food resource. Cambridge University Press, Cambridge, UK."

The invention claimed is:

1. A new and distinct cultivar of the *Ipomoea batatas* (L.) Lam plant named 'CX-1', as described and illustrated herein.

* * * * *